United States Patent [19]

Paul

[11] Plant 4,024

[45] Mar. 22, 1977

[54] DISTINCT VARIETY OF PLUM PLANT

[76] Inventor: Ronald Paul, 5485 E. Heaton, Fresno, Calif. 93727

[21] Appl. No.: 639,261

[22] Filed: Dec. 10, 1975

[51] Int. Cl.[2] ..... A01H 5/03

[52] U.S. Cl. ..... Plt./38

[58] Field of Search ..... Plt./38

*Primary Examiner*—Robert E. Bagwill

*Attorney, Agent, or Firm*—Vergil L. Gerard

EXEMPLARY CLAIM

1. A new and distinct variety of plum substantially as illustrated and described, which is generally similar to the Casselman plum but is distinguishable therefrom primarily by its fruit having a noticably lighter bloom, giving the skin a brighter, darker red color, and by its fruit ripening 3 to 5 days earlier, and being slightly larger and more oblong.

1 Drawing Figure

The present invention relates to a plum tree and more particularly to a new and distinct variety thereof generally similar to a Casselman plum (unpatented) and broadly characterized by its fruit bloom which is less than a Casselman, giving the fruit a brighter, darker red color, and by the fruit being slightly more oblong, larger and ripening three to five days earlier than the Casselman plum.

I discovered the present variety on a farm owned by me at Fresno, Fresno County, Calif., as follows. Several years ago I noticed that one of the Casselman variety (unpatented) plum trees in an orchard on my said farm had a different limb on it. The leaves and blossoms came on the limb at about the same time as on the other limbs, or the other trees in the orchard, however, the leaves were slightly broader. Eventually the limb budded and produced fruit which came on several days earlier than the fruit from other limbs on the tree or on other trees in the orchard. The fruit was substantially identical to the Casselman plum except for its earlier maturity, its being more oblong and slightly larger, and the bloom on the fruit was less, giving the fruit a brighter, darker red color.

Subsequently, I grafted scions from the limb onto Wickson plum root stock. The grafts grew well and ultimately yielded fruit which had characteristics identical to the fruit from the original limb.

The accompanying drawing is a color photographic print of a characteristic whole fruit (three views) of the subject new variety showing the shape and skin color, and a characteristic fruit divided at its suture plane showing the flesh color and pit (two views).

Referring now more specifically to the pomological characteristics of this new and distinct variety of plum tree, the following has been observed under the ecological conditions prevailing near Fresno, Fresno County, Calif., and is an outline description thereof. All major color plate identifications are by reference to Ridgeway, Robert Color Standards and Color Nomenclature, 1912.

TREE

Leaves:

*Shape.*—Shoot leaves: ovate; apex, acuminate; base, acute; Margin, crenate; color, dorsal, Empire Green (Plate XXXII); ventral, Light Blue Green (Plate XVII); ventral surface vein, Absinthe Green to Light Cress Green (Plate XXXI). Spur leaves: obovate; apex, acuminate; base, tapering; margin, crenate; color, same as for shoot leaves.

*Size.*—Shoot leaves: medium size; 5½" long by 2¼" wide; slightly larger than Casselman. Spur leaves: small, 3⅝" by 1¼" wide, thin; slightly larger than Casselman.

*Petiole.*—Shoot leaves: ⅝" to ¾"; medium length and thickness. Spur leaves: to ⅝"; medium slender.

*Glands.*—At base of leaf: none.

*Deciduous.*—Similar to comparative variety.

FLOWERS

Same as Casselman.

FRUIT

Described at maturity:

*Ripening.*—Three to five days earlier than Casselman.

*Size.*—Axially, 2¼"; at right angle to suture plane, 2 5/16"; traverse in suture plane, 2¼"; slightly larger than Casselman.

*Form.*—Globose to broad ovate; slightly more oblong than Casselman.

*Suture.*—A very shallow groove from base to apex; lightly creased in apex; occasionally slightly cracked at shoulder. Similar to Casselman.

*Base.*—Cavity nearly round; medium, flat to narrow, rounded. Similar to Casselman.

*Stem.*—Length ⅜" to ½"; medium stout, 1/16" in diameter; Light Brownish Olive (Plate XXX). Similar to Casselman.

*Skin.*—Thin, moderately tough, tenacious to flesh. Numerous dots; very light bloom; Light Purplish Vinaceous (Plate XXXIX) bloom color; blush color substantially the same as bloom color; ground color similar to Casselman (Chalcedony Yellow, Plate XVII). The difference in color between the new variety and the Casselman plum (the Casselman plum bloom color being Light Mauve (Plate XXV), and its blush color with bloom removed, Napal Red (Plate I) to Bordeaux (Plate XII)) is due principally to the lack of bloom on the new variety. This is its most prominent distinguishing feature.

*Flesh.*—Firm, meaty; even ripening; sprightly flavor; firm; color same as Casselman (Mustard Yellow, Plate XVI).

STONE

Tenacity to flesh: Adheres toward apex; otherwise free.

Color: Warm Buff to Antimony Yellow (Plate XV).

Size: Length ⅞″; breadth ¾″; thickness ⅜″.

SIMILARITY TO PARENT PLANT

My new variety is generally similar to the Casselman plum (unpatented) but has a considerably lighter fruit bloom, giving the fruit a brighter, darker red color. Also, the fruit is slightly more oblong and larger then the Casselman, has a milder flavor, and ripens 3 to 5 days earlier.

a considerably lighter fruit bloom, giving the fruit a brighter, darker red color. Also, the fruit is slightly more oblong and slightly larger than the Casselman, has a milder flavor, and ripens 3 to 5 days earlier.

Distant Markets. Very good shipping quality.

Very good eating quality, milder flavor than parent plant with not so much acidity.

USE

Although my new variety of plum possesses the desired characteristics under the growing conditions near Fresno, Fresno County, Calif., having first been observed there, it is to be understood that variations of the usual magnitude in characteristics incident to the growing conditions, fertilization, pruning and pest control are to be expected.

Having thus described and illustrated my new variety of plum tree, what is claimed is:

1. A new and distinct variety of plum substantially as illustrated and described, which is generally similar to the Casselman plum but is distinguishable therefrom primarily by its fruit having a noticably lighter bloom, giving the skin a brighter, darker red color, and by its fruit ripening 3 to 5 days earlier, and being slightly larger and more oblong.

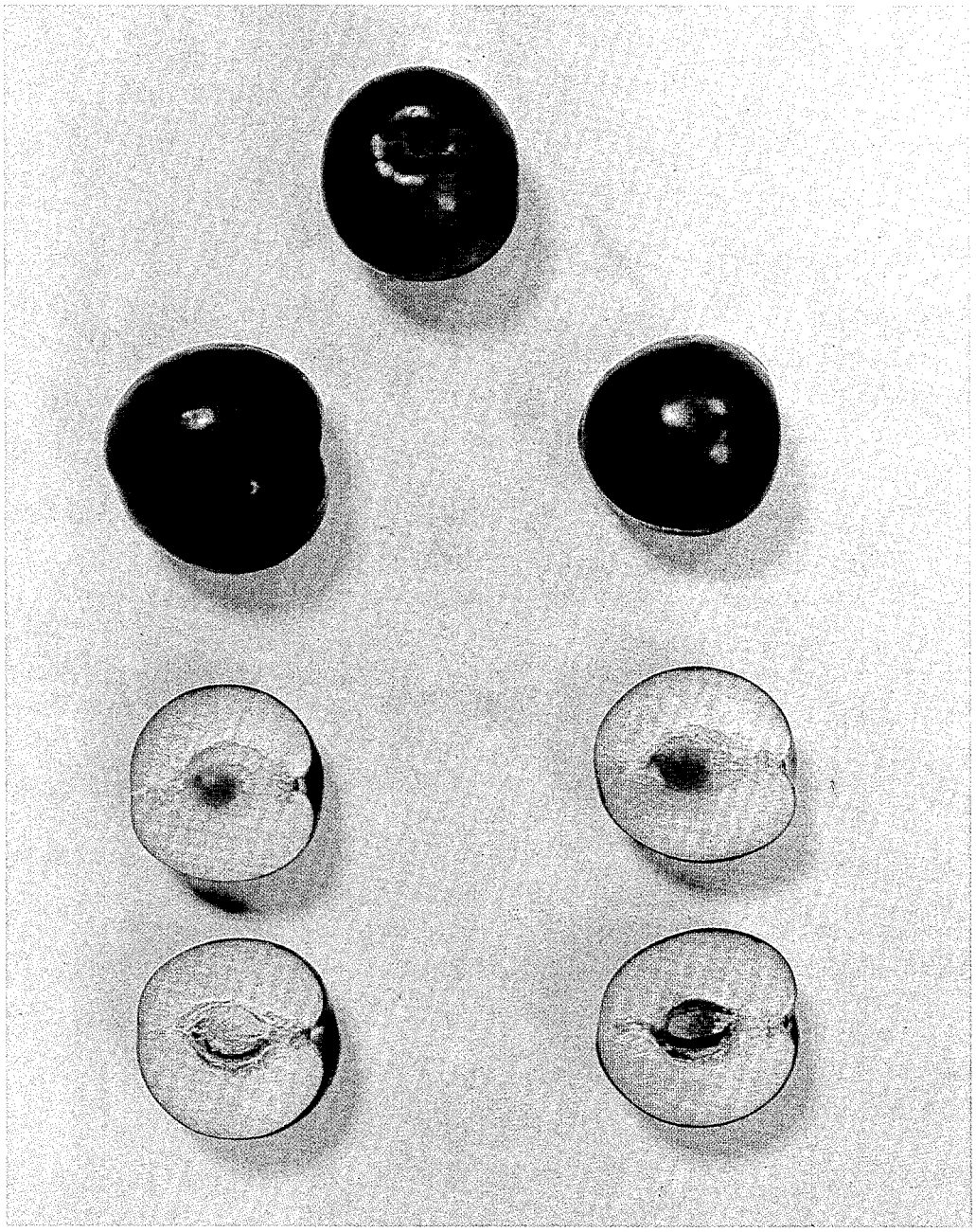

* * * * *